United States Patent
Chapa et al.

(10) Patent No.: US 8,700,169 B1
(45) Date of Patent: Apr. 15, 2014

(54) METHODS AND SYSTEMS FOR REGISTERING AND IDENTIFYING A COCHLEAR IMPLANT EMULATION DEVICE AND MANAGING DATA ASSOCIATED THEREWITH

(75) Inventors: Fernando Chapa, Harold, CA (US); Guillermo A. Calle, Moorpark, CA (US)

(73) Assignee: Advanced Bionics AG, Zug (CH)

( * ) Notice: Subject to any disclaimer, the term of this patent is extended or adjusted under 35 U.S.C. 154(b) by 698 days.

(21) Appl. No.: 12/847,215

(22) Filed: Jul. 30, 2010

(51) Int. Cl.
*A61N 1/05* (2006.01)

(52) U.S. Cl.
USPC .............................. 607/57; 607/137

(58) Field of Classification Search
None
See application file for complete search history.

(56) References Cited

U.S. PATENT DOCUMENTS

| | | | | |
|---|---|---|---|---|
| 2004/0208330 A1* | 10/2004 | Chalupper et al. | | 381/314 |
| 2006/0084848 A1* | 4/2006 | Mitchnick | | 600/301 |
| 2007/0135862 A1* | 6/2007 | Nicolai et al. | | 607/56 |
| 2007/0208403 A1* | 9/2007 | Della Santina et al. | | 607/137 |
| 2007/0230711 A1* | 10/2007 | Hasler et al. | | 381/58 |
| 2007/0255344 A1* | 11/2007 | Van Dijk | | 607/57 |
| 2009/0006860 A1* | 1/2009 | Ross | | 713/189 |

FOREIGN PATENT DOCUMENTS

WO  WO 2007090243 A1 *  8/2007

* cited by examiner

*Primary Examiner* — Brian T Gedeon
*Assistant Examiner* — Ankit Tejani
(74) *Attorney, Agent, or Firm* — ALG Intellectual Property, LLC (57) ABSTRACT

An exemplary method includes a cochlear implant fitting subsystem maintaining patient data associated with a cochlear implant patient, maintaining registration data for a cochlear implant emulation device registered with the fitting subsystem and configured to emulate an implanted cochlear device, detecting a coupling of a cochlear implant device to the fitting subsystem, automatically determining, based on the registration data, that the coupled cochlear implant device is the cochlear implant emulation device registered with the fitting subsystem, performing one or more operations while the cochlear implant emulation device is coupled to the fitting subsystem, and preventing data acquired by the fitting subsystem during the performance of the one or more operations while the cochlear implant emulation device is coupled to the fitting subsystem from being included in the patient data. Corresponding methods and systems are also described.

13 Claims, 9 Drawing Sheets

METHODS AND SYSTEMS FOR REGISTERING AND IDENTIFYING A COCHLEAR IMPLANT EMULATION DEVICE AND MANAGING DATA ASSOCIATED THEREWITH

BACKGROUND INFORMATION

The natural sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers by way of one or more channels formed by an array of electrodes implanted in the cochlea. Direct stimulation of the auditory nerve fibers leads to the perception of sound in the brain and at least partial restoration of hearing function.

When a cochlear implant of a cochlear implant system is initially implanted in a patient, and during follow-up tests and checkups thereafter, it is usually necessary to fit the cochlear implant system to the patient. Fitting of a cochlear implant system to a patient is typically performed by an audiologist or the like who utilizes a fitting system to present various stimuli to the patient and relies on subjective feedback from the patient as to how such stimuli are perceived.

The audiologist or the like may further utilize the fitting system to perform diagnostic and/or troubleshooting procedures on a cochlear implant system. For example, if a cochlear implant system stops working correctly, the fitting system may be utilized to troubleshoot the cochlear implant system. During troubleshooting, a cochlear implant emulation device may be substituted for an implanted cochlear device in the cochlear implant system in order to determine whether the implanted cochlear implant is the source of a problem. This is typically accomplished by the audiologist or the like uncoupling the implanted cochlear device from a component of the cochlear implant system and coupling a cochlear implant emulation device configured to emulate the implanted cochlear device to the component.

A cochlear implant emulation device typically includes an implantable cochlear device bundled with a resistive load intended to help the implantable cochlear device emulate conditions of an implanted cochlear implant device. Because the cochlear implant emulation device is designed to operate as much like an implanted cochlear implant device as possible, a conventional fitting system is unable to distinguish the cochlear implant emulation device from the implanted cochlear implant device. While this is a desirable characteristic for diagnosing and/or troubleshooting the cochlear implant system, the inability of the fitting system to distinguish between the cochlear implant emulation device and the implanted cochlear implant device can undesirably affect certain operations of the fitting system. For example, patient data maintained by the fitting system may be inadvertently polluted with data gathered from and representative of characteristics (e.g., impedance values) of the cochlear implant emulation device. Unfortunately, because the characteristics of the cochlear implant emulation device may be different from characteristics of the implanted cochlear implant device, once data gathered from the cochlear implant emulation device is mingled with the patient data, the characteristics of the cochlear implant emulation device will undesirably affect computations performed by fitting subsystem, such as computations performed to fit the implanted cochlear implant device to a patient.

SUMMARY

An exemplary method includes a cochlear implant fitting subsystem 1) maintaining patient data associated with a cochlear implant patient, 2) maintaining registration data for a cochlear implant emulation device registered with the fitting subsystem and configured to emulate an implanted cochlear device, 3) detecting a coupling of a cochlear implant device to the fitting subsystem, 4) automatically determining, based on the registration data, that the coupled cochlear implant device is the cochlear implant emulation device registered with the fitting subsystem, 5) performing one or more operations while the cochlear implant emulation device is coupled to the fitting subsystem, and 6) preventing data acquired by the fitting subsystem during the performance of the one or more operations while the cochlear implant emulation device is coupled to the fitting subsystem from being included in the patient data.

Another exemplary method includes a cochlear implant fitting subsystem 1) receiving a request to register a cochlear implant emulation device with the fitting subsystem, 2) initiating, in response to the request, a registration process, 3) obtaining, via the coupling, a unique identifier for the cochlear implant emulation device during the registration process, and 4) registering the cochlear implant emulation device with the fitting subsystem during the registration process, the registering including storing the unique identifier in registration data maintained by the fitting subsystem.

An exemplary system includes a registration facility that maintains registration data for a registered cochlear implant emulation device configured to emulate an implanted cochlear device. The system further includes a fitting facility communicatively coupled to the registration facility and configured to maintain patient data associated with a cochlear implant patient, detect a coupling of a cochlear implant device, automatically determine, based on the registration data, that the coupled cochlear implant device is the registered cochlear implant emulation device, perform one or more operations while the cochlear implant emulation device is coupled, and prevent data acquired by the fitting facility during the performance of the one or more operations while the cochlear implant emulation device is coupled from being included in the patient data.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Methods and systems for managing a cochlear implant device and data associated therewith are disclosed. More particularly, methods and systems for registering and identifying a cochlear implant emulation device and managing data associated therewith are described herein. As described in more detail below, a fitting subsystem may be configured to receive a request to register a cochlear implant emulation device with the fitting subsystem. The fitting subsystem may initiate, in response to the request, a registration process, obtain a unique identifier for the cochlear implant emulation device, and register the cochlear implant emulation device with the fitting subsystem such as by storing the unique identifier in registration data maintained by the fitting subsystem.

Subsequently, the fitting subsystem may detect a coupling of a cochlear implant device to the fitting subsystem and automatically determine, based on the registration data, that the coupled cochlear implant device is the cochlear implant emulation device registered with the fitting subsystem. The fitting subsystem may perform one or more operations while the cochlear implant emulation device is coupled to the fitting subsystem and prevent data acquired by the fitting subsystem during the performance of the one or more operations while the cochlear implant emulation device is coupled to the fitting subsystem from being included in patient data maintained by the fitting subsystem.

Numerous advantages may be associated with the methods and systems described herein. For example, by being able to distinguish a registered cochlear implant emulation device from an actual implanted cochlear device, a fitting subsystem (e.g., a fitting station utilized by an audiologist) may manage data associated with the actual implanted cochlear device and the cochlear implant emulation device selectively, including preventing data associated with the cochlear implant emulation device (e.g., data representative of one or more characteristics of the cochlear implant emulation device) from being included in patient data. Conversely, data associated with the actual implanted cochlear device (e.g., data representative of one or more characteristics of the actual implanted cochlear device) may be included in patient data. In this manner, pollution of patient data with data that is associated with a cochlear implant emulation device may be avoided.

As used herein, the term "implanted cochlear device" refers to an implantable cochlear device (e.g., an implantable cochlear stimulator) that is implanted in a patient. An implanted cochlear device may also be referred to herein as a "patient implant." The term "cochlear implant emulation device," as used herein, refers to an implantable cochlear device that is not implanted in a patient but that is configured to emulate an implanted cochlear device. For example, a cochlear implant emulation device may include an implantable cochlear device (e.g., an implantable cochlear stimulator) bundled with a resistive load. A cochlear implant emulation device may also be referred to herein as a "reference implant." The term "cochlear implant device," as used herein, may refer to an implanted cochlear device or a cochlear implant emulation device.

Figure 1:
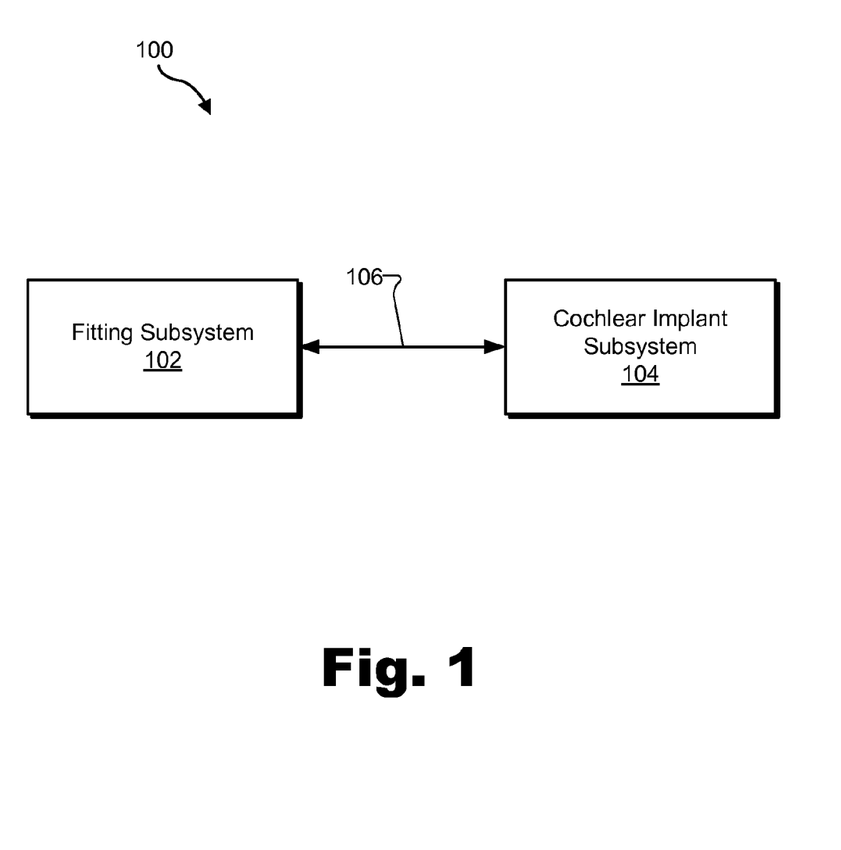
FIG. 1 illustrates an exemplary cochlear implant management system according to principles described herein.

To facilitate an understanding of the methods and systems described herein, an exemplary cochlear implant management system 100 will be described in connection with FIG. 1. As shown in FIG. 1, cochlear implant management system 100 may include a fitting subsystem 102 and a cochlear implant subsystem 104. Fitting subsystem 102 may be configured to be selectively and communicatively coupled to cochlear implant subsystem 104 by way of a communication link 106. Fitting subsystem 102 and cochlear implant subsystem 104 may communicate using any suitable communication technologies, devices, networks, media, and protocols supportive of data communications.

Figure 2:
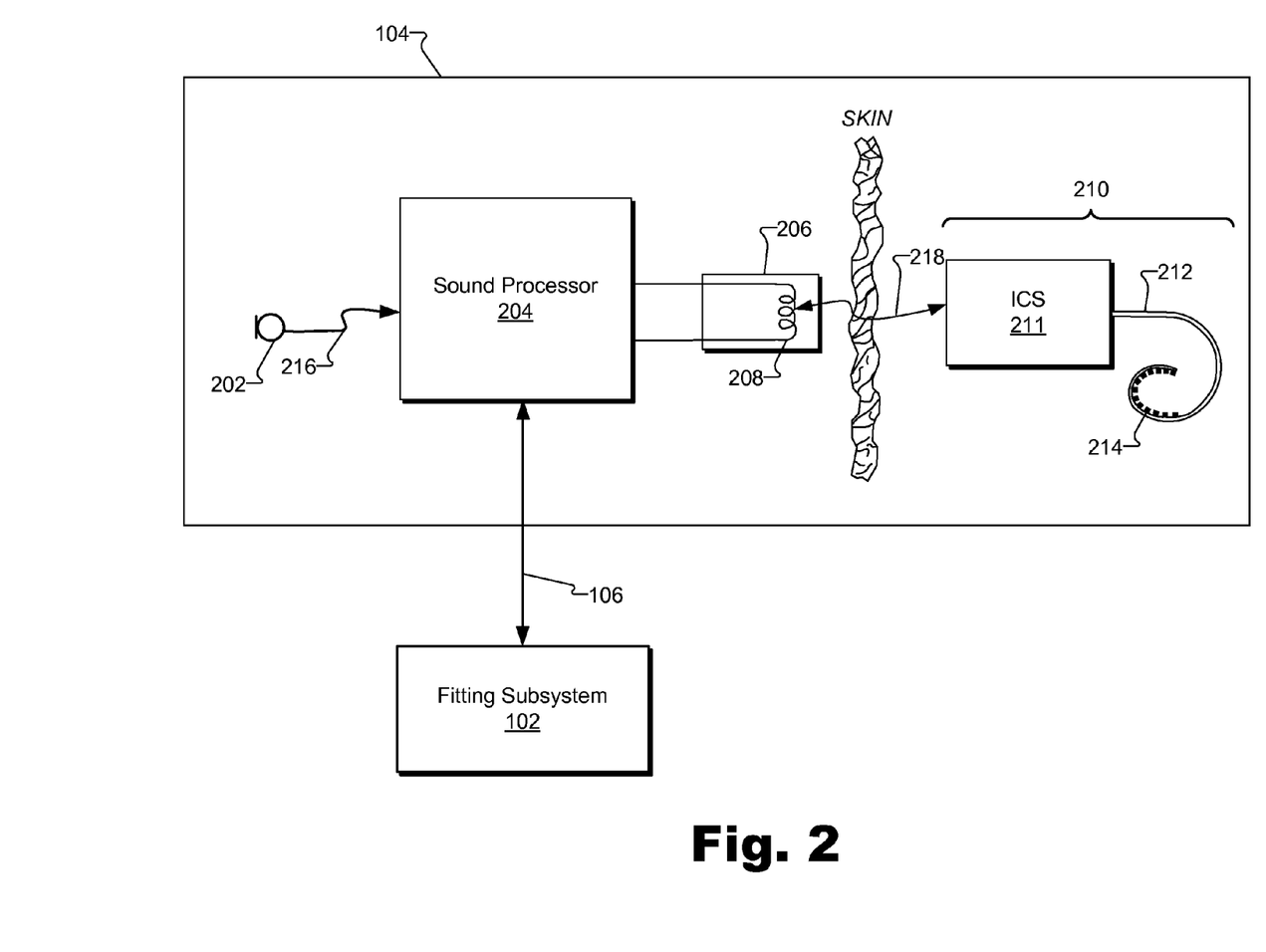
FIG. 2 illustrates an exemplary cochlear implant subsystem including an implanted cochlear device according to principles described herein.

Cochlear implant subsystem 104 may include one or more components configured to convert an audio signal to an electrical signal and to generate one or more stimulation signals based on the electrical signal. The stimulation signals may be configured to stimulate auditory nerve fibers of a patient to produce a perception of sound in the brain of the patient. FIG. 2 illustrates exemplary components of cochlear implant subsystem 104. As shown in FIG. 2, cochlear implant subsystem 104 may include a microphone 202, a sound processor 204, a headpiece 206 having a coil 208 disposed therein, and an implanted cochlear device 210 comprising an implantable cochlear stimulator ("ICS") 211 and a lead 212 with a plurality of electrodes 214 disposed thereon. Additional or alternative components may be included within cochlear implant subsystem 104 as may serve a particular implementation.

As shown in FIG. 2, microphone 202, sound processor 204, and headpiece 206 may be located external to a cochlear implant patient, and implanted cochlear device 210 is implanted subcutaneously with a patient. In some alternative examples, microphone 202 and/or sound processor 204 may be implanted within the patient. In such configurations, the need for headpiece 206 may be obviated.

Microphone 202 may detect an audio signal and convert the detected signal to a corresponding electrical signal. The electrical signal may be sent from microphone 202 to sound processor 204 via a communication link 216, which may include a telemetry link, a wire, and/or any other suitable communication link.

Sound processor 204 is configured to direct implantable cochlear stimulator 211 to generate and apply electrical stimulation (also referred to herein as "stimulation current") to one or more stimulation sites within a cochlea of the patient. To this end, sound processor 204 may process the audio signal detected by microphone 202 in accordance with a selected sound processing strategy to generate appropriate stimulation parameters for controlling implantable cochlear stimulator 211. Sound processor 204 may include or be implemented by a behind-the-ear ("BTE") unit, a portable speech processor ("PSP"), and/or any other sound processing unit as may serve a particular implementation.

Sound processor 204 may be configured to transcutaneously transmit one or more control parameters and/or one or more power signals to implantable cochlear stimulator 211 with coil 208 by way of a communication link 218. These control parameters may be configured to specify one or more stimulation parameters, operating parameters, and/or any other parameter by which implantable cochlear stimulator 211 is to operate as may serve a particular implementation. Exemplary control parameters include, but are not limited to, stimulation current levels, volume control parameters, program selection parameters, operational state parameters (e.g., parameters that turn a sound processor and/or an implantable cochlear stimulator on or off), audio input source selection parameters, fitting parameters, testing parameters, diagnostic parameters, troubleshooting parameters, noise reduction parameters, microphone sensitivity parameters, microphone direction parameters, pitch parameters, timbre parameters, sound quality parameters, most comfortable current levels ("M levels"), threshold current levels, channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Sound processor 204 may also be configured to operate in accordance with one or more of the control parameters.

As shown in FIG. 2, coil 208 may be housed within headpiece 206, which may be affixed to a patient's head and positioned such that coil 208 is communicatively coupled to a corresponding coil included within implantable cochlear stimulator 211. In this manner, control parameters and power signals may be wirelessly transmitted between sound processor 204 and implantable cochlear stimulator 211 via communication link 218. It will be understood that data communication link 218 may include a bi-directional communication link and/or one or more dedicated uni-directional communication links. In some alternative embodiments, sound processor 204 and implantable cochlear stimulator 211 may be directly connected with one or more wires or the like.

Implantable cochlear stimulator 211 may be configured to generate electrical stimulation representative of an audio signal detected by microphone 202 in accordance with one or more stimulation parameters transmitted thereto by sound processor 204. Implantable cochlear stimulator 211 may be further configured to apply the electrical stimulation to one or more stimulation sites within the cochlea via one or more electrodes 214 disposed along lead 212. In some examples, implantable cochlear stimulator 211 may include a plurality of independent current sources each associated with a channel defined by one or more of electrodes 214. In this manner, different stimulation current levels may be applied to multiple stimulation sites simultaneously by way of multiple electrodes 214. In such examples, cochlear implant subsystem 204 may be referred to as a "multi-channel cochlear implant system."

To facilitate application of the electrical stimulation generated by implantable cochlear stimulator 211, lead 212 may be inserted within a duct of the cochlea such that electrodes 214 are in communication with one or more stimulation sites within the cochlea. As used herein, the term "in communication with" refers to electrodes 214 being adjacent to, in the general vicinity of, in close proximity to, directly next to, or directly on the stimulation site. Any number of electrodes 214 (e.g., sixteen) may be disposed on lead 212 as may serve a particular implementation.

During normal operation, cochlear implant subsystem 104 is typically decoupled from fitting subsystem 102. However, cochlear implant subsystem 104 may be coupled to fitting subsystem 102 by way of communication link 106 as shown in FIG. 2 such that fitting subsystem 104 may perform one or more of the operations on cochlear implant subsystem 104, including, but not limited to, one or more fitting operations, testing operations, diagnostic operations, and/or troubleshooting operations.

For example, during normal operation, cochlear implant subsystem 104 may stop functioning correctly. Cochlear implant subsystem 104 may be coupled to fitting subsystem 102 by communication link 106 as shown in FIG. 2 such that fitting subsystem 102 may perform one or more diagnostic and/or troubleshooting operations on cochlear implant subsystem 104. Diagnostic and/or troubleshooting operations may be designed to identify a source of a problem with cochlear implant subsystem 104. For example, as shown in FIG. 2, cochlear implant subsystem 104 may include multiple components, and diagnostic and/or troubleshooting operations may be designed to identify which component or components may be causing a particular problem.

To illustrate, as part of diagnostic and/or troubleshooting operations, a user of fitting subsystem 102 (e.g., an audiologist, clinician, product quality tester, manufacturer, or the like) may substitute implanted cochlear device 210 with a working cochlear implant emulation device configured to emulate implanted cochlear device 210. The substitution may be accomplished in any suitable way. Typically, the substitution includes the user decoupling headpiece 206 from implantable cochlear stimulator 211 (e.g., by physically moving headpiece 206 away from implantable cochlear stimulator 211) and coupling headpiece 206 to the cochlear implant emulation device that is not implanted in a patient (e.g., by physically moving headpiece 206 proximate to the cochlear implant emulation device such that a communication link is established between headpiece 206 and the cochlear implant emulation device).

Figure 3:
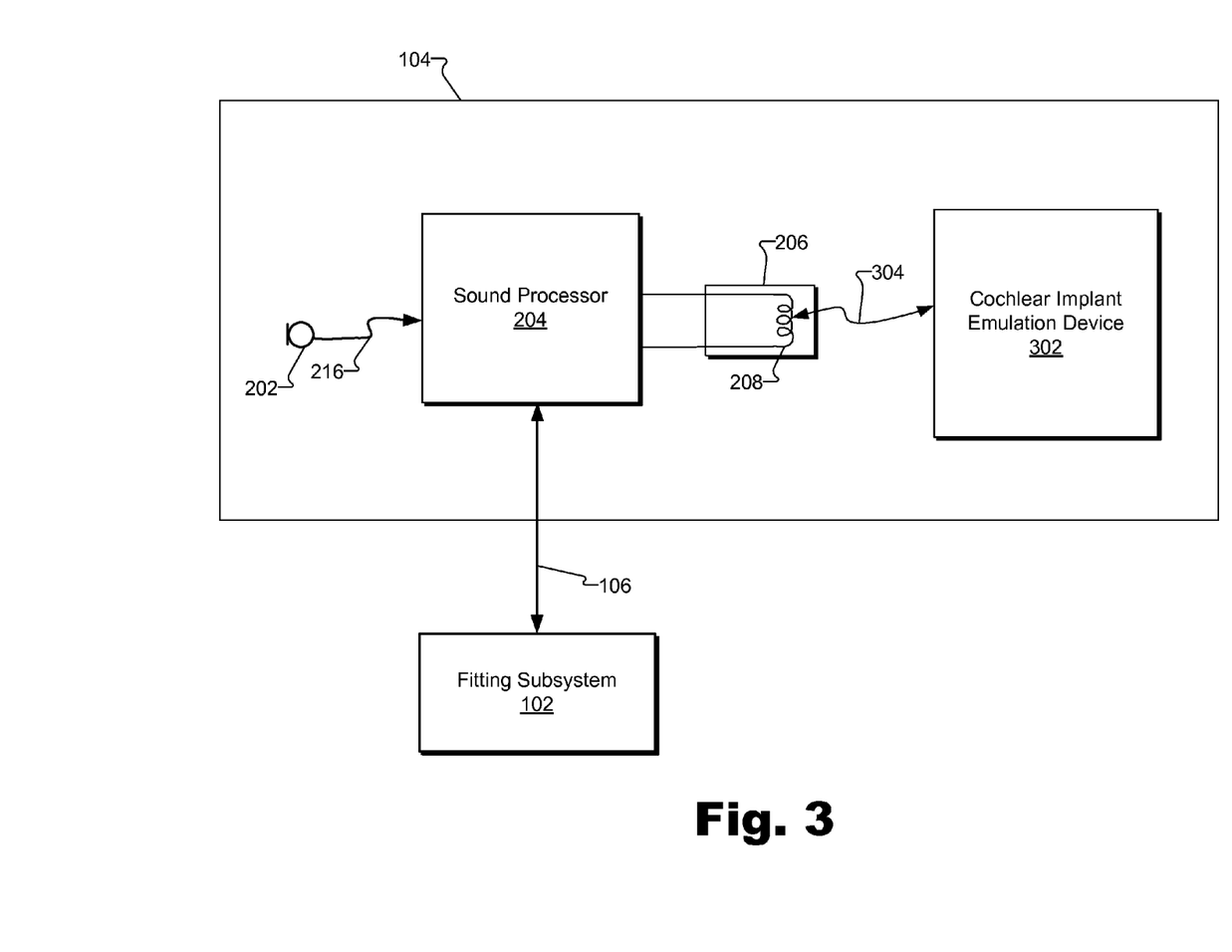
FIG. 3 illustrates an exemplary cochlear implant subsystem including a cochlear implant emulation device according to principles described herein.

For example, FIG. 3 illustrates cochlear implant subsystem 104 including a cochlear implant emulation device 302 coupled to headpiece 206 by a communication link 304. Cochlear implant emulation device 302 may include one or more components configured to emulate implanted cochlear device 210. In certain examples, cochlear implant emulation device 302 may include a working implantable cochlear stimulator that is not implanted in a patient and that is bundled with a resistive load designed to help the working implantable cochlear stimulator emulate conditions and/or characteristics of implanted cochlear device 210.

A coupling of cochlear implant emulation device 302 to headpiece 206 in place of implantable cochlear device 210 may be desirable for one or more diagnostic and/or troubleshooting operations. For example, with cochlear implant emulation device 302 coupled to headpiece 206 as shown in FIG. 3, fitting subsystem 102 may perform one or more troubleshooting operations on cochlear implant subsystem 104. If the one or more troubleshooting operations indicate that cochlear implant subsystem 104 functions incorrectly while implanted cochlear device 210 is coupled to fitting subsystem 102 (by way of communication link 218 with headpiece 206 and communication link 106 with sound processor 204) and correctly while cochlear implant emulation device 302 is coupled to fitting subsystem 102 (by way of communication link 304 with headpiece 206 and communication link 106 with sound processor 204), a user of fitting subsystem 102 may deduce that there is a problem with implanted cochlear device 210.

While coupling cochlear implant emulation device 302 to headpiece 206 may be helpful for diagnosing and/or troubleshooting cochlear implant subsystem 104, as mentioned above, such a configuration may introduce undesirable data and/or consequences into a conventional cochlear implant fitting system that is unable to distinguish between an implanted cochlear device and a cochlear implant emulation device that is not implanted in a patient but is configured to emulate an implanted cochlear device. However, fitting subsystem 102 is configured to avoid such undesirable consequences. For example, fitting subsystem 102 is configured to distinguish between an implanted cochlear device (e.g., implanted cochlear device 210) and a cochlear implant emulation device (e.g., cochlear implant emulation device 302) that is not implanted in a patient but that is configured to emulate an implanted cochlear device. In addition, when fitting subsystem 102 determines that a cochlear implant emulation device is coupled to headpiece 206 in cochlear implant subsystem 104, fitting subsystem 102 may process data associated with one or more operations performed while the cochlear implant emulation device is coupled to headpiece 206 differently than data associated with one or more operations performed while an implanted cochlear device is coupled to headpiece 206.

To illustrate, data associated with one or more operations performed while an implanted cochlear device is coupled to headpiece 206 may be gathered and added to patient data maintained by fitting subsystem 102. As an example, an impedance value associated with the implanted cochlear device may be measured and added to patient data associated with a patient. Subsequently, the patient data may be utilized in one or more fitting operations to fit the implanted cochlear device to the patient such that the impedance value included in the patient data may be taken into account. This is desirable because the measured impedance of the implanted cochlear device may be helpful to fit the implanted cochlear device to the patient.

Conversely, data associated with one or more operations performed while the cochlear implant emulation device is coupled to headpiece 206 may be prevented from being included in patient data associated with the patient. As an example, an impedance value associated with the cochlear implant emulation device may be measured. However, an impedance value associated with a cochlear implant emulation device may be different from an impedance value associated with an implanted cochlear device. For instance, the impedance value associated with the cochlear implant emulation device may be set to a nominal value because the cochlear implant emulation device is tied to a resistive load configured to emulate the actual load of the implanted cochlear device. Therefore, it would not be desirable to add the impedance value associated with the cochlear implant emulation device to patient data at least because doing so may lead to the use of data not associated with the implanted cochlear device when the patient data is used in one or more fitting operations to fit the implanted cochlear device to the patient.

Figure 4:
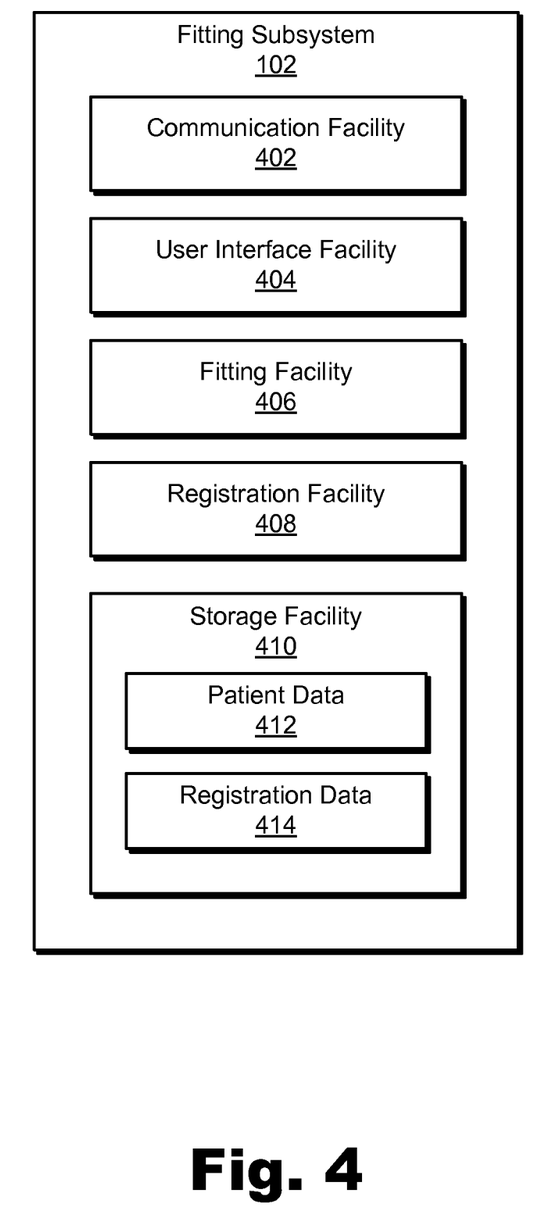
FIG. 4 illustrates exemplary components of an exemplary fitting subsystem according to principles described herein.

To further facilitate an understanding of fitting subsystem 102, FIG. 4 illustrates exemplary components of fitting subsystem 102. Fitting subsystem 102 may be implemented by any suitable combination of computing and communication devices including, but not limited to, a fitting station, a personal computer, a laptop computer, a handheld device, a mobile device (e.g., a mobile phone), a clinician's programming interface ("CPI") device, and/or any other suitable component as may serve a particular implementation.

As shown in FIG. 4, fitting subsystem 102 may include a communication facility 402, a user interface facility 404, a fitting facility 406, a registration facility 408, and a storage facility 410, which may be communicatively coupled to one another using any suitable communication technologies. Each of these facilities will now be described in more detail.

Communication facility 402 may be configured to facilitate communication between fitting subsystem 102 and cochlear implant subsystem 104. For example, communication facility 402 may be implemented by a CPI device, which may include any suitable combination of components configured to allow fitting subsystem 102 to interface and communicate with sound processor 204 of cochlear implant subsystem 104. Communication facility 402 may additionally or alternatively include one or more transceiver components configured to wirelessly transmit data (e.g., program data and/or control parameter data) to sound processor 204 and/or wirelessly receive data (e.g., feedback data, impedance measurement data, neural response data, etc.) from sound processor 204. Communication facility 402 may additionally or alternatively be configured to facilitate communication between fitting subsystem 102 and one or more other devices (e.g., by way of the Internet and/or one or more other types of networks) as may serve a particular implementation.

User interface facility 404 may be configured to provide one or more user interfaces configured to facilitate user interaction with fitting subsystem 102. For example, user interface facility 404 may provide a graphical user interface ("GUI") through which one or more functions, options, features, and/or tools associated with one or more operations described herein may be provided to a user and through which user input may be received. In certain embodiments, user interface facility 404 may be configured to provide the GUI (e.g., a device registration GUI) to a display device (e.g., a computer monitor) for display.

Fitting facility 406 may be configured to perform one or more operations on and/or otherwise related to cochlear implant subsystem 104, including one or more fitting, testing, diagnostic, and/or troubleshooting operations described herein. For example, fitting facility 406 may be configured to adjust one or more control parameters by which cochlear implant subsystem 104 operates, direct cochlear implant subsystem 104 to measure one or more characteristics of cochlear implant subsystem 104 (e.g., electrode impedances), perform one or more neural response detection operations, and/or perform one or more additional or alternative fitting, testing, diagnostic, and/or troubleshooting operations.

As part of one or more operations performed by fitting facility 406, fitting facility 406 may acquire data from cochlear implant subsystem 104 during performance of the operations. For example, fitting facility 406 may acquire measured characteristics (e.g., electrode impedances) of cochlear implant subsystem 104 during performance of one or more operations.

Fitting facility 406 may be configured to maintain patient data associated with one or more cochlear implant patients. The patient data may be stored as patient data 412 in storage facility 410. The patient data may include any information associated with a patient and/or one or more components of a cochlear implant subsystem 104 associated with the patient.

For example, the patient data may include control parameters, settings, and characteristics of the cochlear implant subsystem 104. Fitting facility 406 may utilize the patient data in one or more operations performed by fitting facility 406. For example, fitting facility 406 may utilize the patient data in one or more fitting operations to fit an implanted cochlear device to a patient.

Fitting facility 406 may be configured to detect a coupling of a cochlear implant device to fitting subsystem 102. For example, when communication facility 402 of fitting subsystem 102 is coupled to sound processor 204 by way of communication link 106 and a cochlear implant device is coupled to headpiece 206, a communication path may be formed between fitting subsystem 102 and the cochlear implant device (e.g., implanted cochlear device 210 or cochlear implant emulation device 302) by way of communication link 106, sound processor 204, headpiece 206, and communication link 218 or 304 as shown in FIG. 2 or FIG. 3, respectively. The communication path, which may be referred to as a coupling of the cochlear implant device to fitting subsystem 102, may be detected by fitting facility 406 in any suitable way.

Fitting facility 406 may be configured to automatically determine, in response to a detected coupling of a cochlear implant device to fitting subsystem 102, whether the cochlear implant device is an implanted cochlear device or a cochlear implant emulation device. In certain embodiments, for example, fitting facility 406 may utilize registration data representative of one or more reference cochlear implant devices pre-registered with fitting subsystem 102 to determine whether the coupled cochlear implant device is registered with the fitting subsystem 102 (e.g., by searching the registration data for a match to a unique identifier associated with the coupled cochlear implant device). If fitting facility 406 determines, based on the registration data, that the coupled cochlear implant device is registered with the fitting subsystem 102, fitting facility 406 may adjust performance of one or more operations accordingly. For example, fitting facility 406 may prevent data acquired during performance of one or more operations while the registered cochlear implant emulation device is coupled to fitting subsystem 102 from being included in (e.g., from being added to) patient data maintained by fitting facility 406. Conversely, if fitting facility 406 determines, based on the registration data, that the coupled cochlear implant device is not registered with the fitting subsystem 102, fitting facility 406 may perform one or more operations accordingly. For example, fitting facility 406 may add data acquired during performance of one or more operations while the unregistered cochlear implant device is coupled to fitting subsystem 102 to patient data maintained by fitting facility 406.

Registration facility 408 may be configured to register reference cochlear implants with fitting subsystem 102. To this end, registration facility 408 may provide one or more tools configured to facilitate registration of a reference cochlear implant with fitting subsystem 102. For example, registration facility 408 may provide data representative of one or more graphical user interfaces ("GUIs") and/or GUI tools to user interface facility 404 for use in rendering one or more registration GUIs, examples of which are described further below.

Registration facility 408 may be configured to receive a request to register a cochlear implant emulation device with fitting subsystem 102. For example, user input indicating a request may be provided by a user and received by registration facility 408 by way of a GUI. In response to the request, registration facility 408 may initiate a registration process and perform one or more registration operations as part of the process. In certain examples, the registration operations may include obtaining a unique identifier for the cochlear implant emulation device to be registered and registering the cochlear implant emulation device with fitting subsystem 102 such as by storing the unique identifier in registration data maintained by registration facility 408. Examples of registration operations are described below.

Registration facility 408 may be configured to maintain registration data representative of one or more cochlear implant emulation devices registered with fitting subsystem 102. The registration data, which may be stored as registration data 414 in storage facility 410, may include any data that may be used by fitting facility 406 to identify one or more cochlear implant emulation devices registered with fitting subsystem 102. In certain examples, the registration data may include a unique identifier for each cochlear implant emulation device registered with fitting subsystem 102. In some examples, a cochlear implant device may maintain data representative of a unique identifier, and registration facility 408 may be configured to obtain the unique identifier from the cochlear implant device when the cochlear implant device is coupled to fitting subsystem 102. To register a cochlear implant emulation device with fitting subsystem 102, registration facility 408 may obtain and add the unique identifier for the cochlear implant emulation device to the registration data.

Storage facility 410 may be configured to maintain patient data 412 and registration data 414. Storage facility 410 may be configured to maintain additional or alternative data as may serve a particular implementation. For example, storage facility 410 may store program data representative of one or more sound processing programs and/or control parameter data representative of one or more control parameters to be used in one or more operations performed by fitting subsystem 102.

Figure 5:
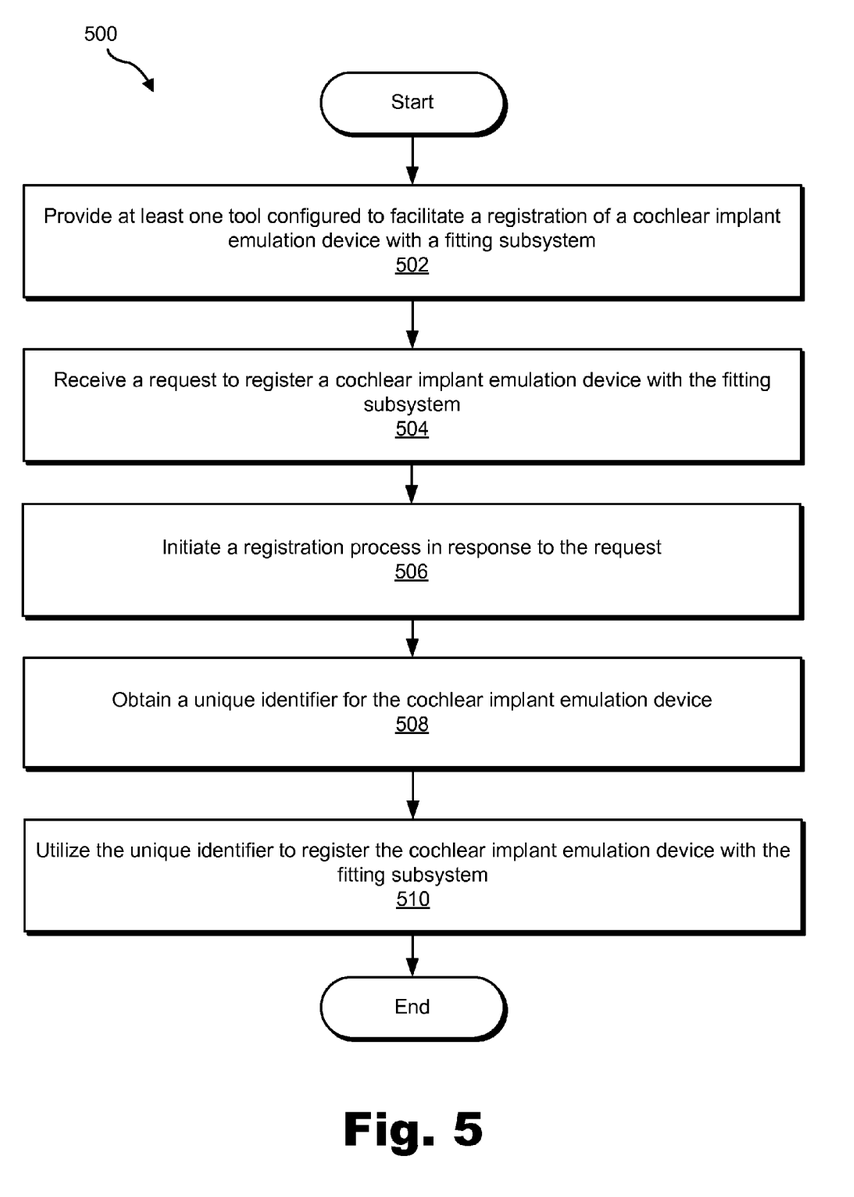
FIG. 5 illustrates an exemplary method of registering a cochlear implant emulation device according to principles described herein.

FIG. 5 illustrates an exemplary method 500 of registering a cochlear implant emulation device. While FIG. 5 illustrates exemplary steps according to one embodiment, other embodiments may omit, add to, reorder, combine, and/or modify any of the steps shown in FIG. 5. One or more of the steps shown in FIG. 5 may be performed by any component or combination of components of fitting subsystem 102.

In step 502, fitting subsystem 102 may provide at least one tool configured to facilitate a registration of a cochlear implant emulation device with fitting subsystem 102. For example, fitting subsystem 102 may provide one or more GUIs and/or GUI tools for use by a user of fitting subsystem 102 to initiate registration of a cochlear implant emulation device with fitting subsystem 102. Exemplary registration GUIs are described further below in reference to FIGS. 6-7.

In step 504, fitting subsystem 102 may receive a request to register a cochlear implant emulation device with fitting subsystem 102. The request may be provided and received in any suitable way. For example, the request may be provided and/or received through a registration GUI, such as by a user selecting an option in the GUI configured to initiate a registration of a cochlear implant emulation device with fitting subsystem 102. As another example, the request may include fitting subsystem 102 detecting a coupling of a cochlear implant emulation device to fitting subsystem 102 and determining that the coupled cochlear implant emulation device has not been previously coupled to fitting subsystem 102. This determination may be made in any suitable way, such as by fitting subsystem 102 retrieving a unique identifier from the coupled cochlear implant emulation device and searching data maintained by fitting subsystem 102 to determine that the unique identifier is not included in the data.

In step 506, fitting subsystem 102 may initiate a registration process in response to the request. The registration process may include performance of one or more registration operations, including any of the registration operations described herein, configured to facilitate registration of a cochlear implant emulation device with fitting subsystem 102.

In step 508, fitting subsystem 102 may obtain a unique identifier for the cochlear implant emulation device during the registration process. The unique identifier may be obtained in any suitable way. As an example, fitting subsystem 102 may prompt a user to enter the unique identifier into a registration GUI. As another example, if the cochlear implant emulation device is coupled to fitting subsystem 102, fitting subsystem 102 may detect the coupling during the registration process and, in response to the detection, request and acquire data representative of the unique identifier from the cochlear implant emulation device by way of the coupling. As yet another example, if the cochlear implant emulation device is not coupled to fitting subsystem 102 during the registration process, fitting subsystem 102 may prompt, during the registration process, a user to perform an action to facilitate an establishment of a coupling of the cochlear implant emulation device to fitting subsystem 102. For instance, the user may be prompted to physically establish a connection between the cochlear implant emulation device and fitting subsystem 102 or one or more components of cochlear implant subsystem 104 to which fitting subsystem 102 is coupled by way of communication link 106. With the cochlear implant emulation device coupled to fitting subsystem 102, fitting subsystem 102 may request and acquire data representative of the unique identifier from the cochlear implant emulation device by way of the coupling.

In step 510, fitting subsystem 102 may utilize the unique identifier obtained in step 508 to register the cochlear implant emulation device with fitting subsystem 102 during the registration process. In certain examples, this may be accomplished by storing the unique identifier in registration data maintained by fitting subsystem 102.

Figure 6:
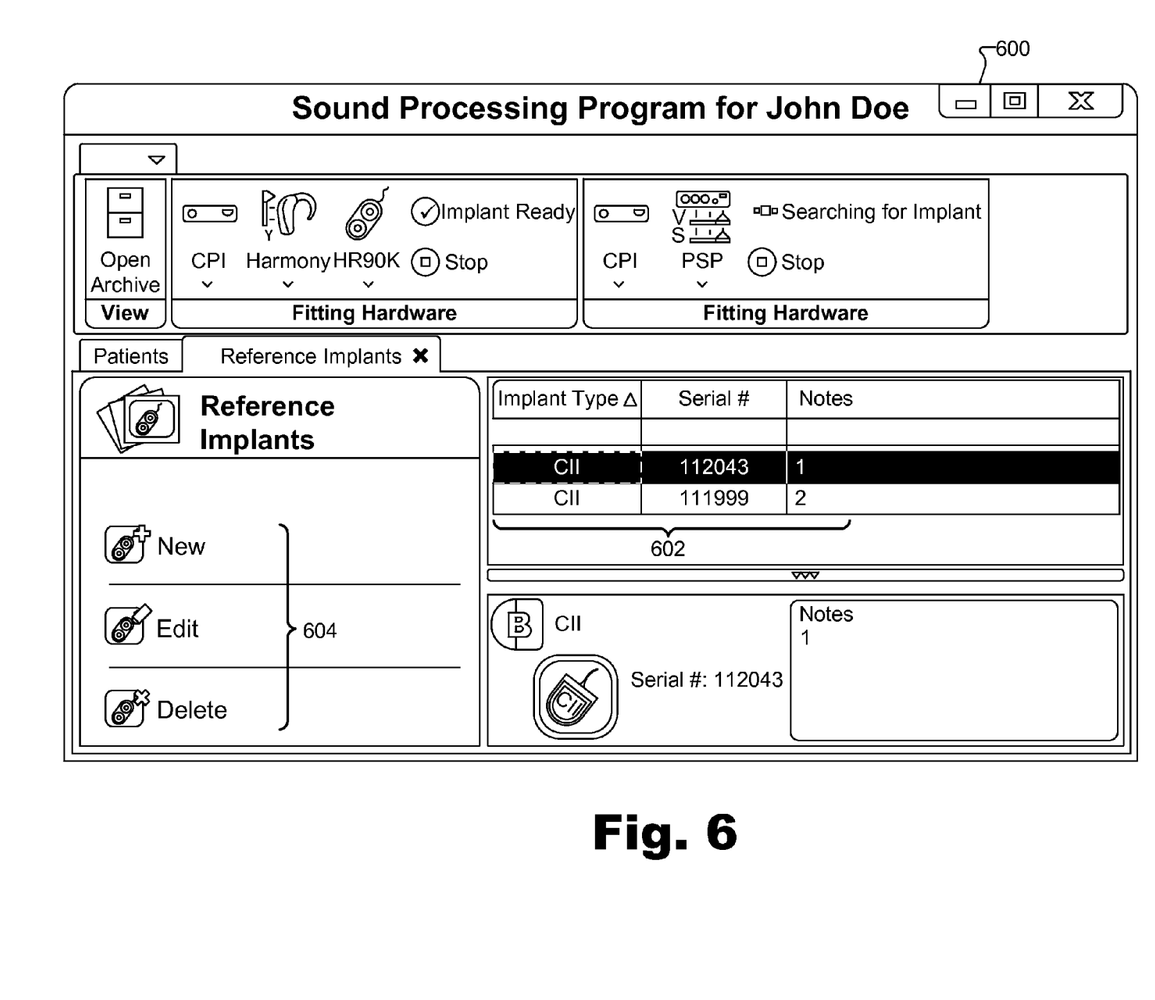
FIGS. 6-7 illustrate exemplary registration graphical user interfaces according to principles described herein.
Figure 7:
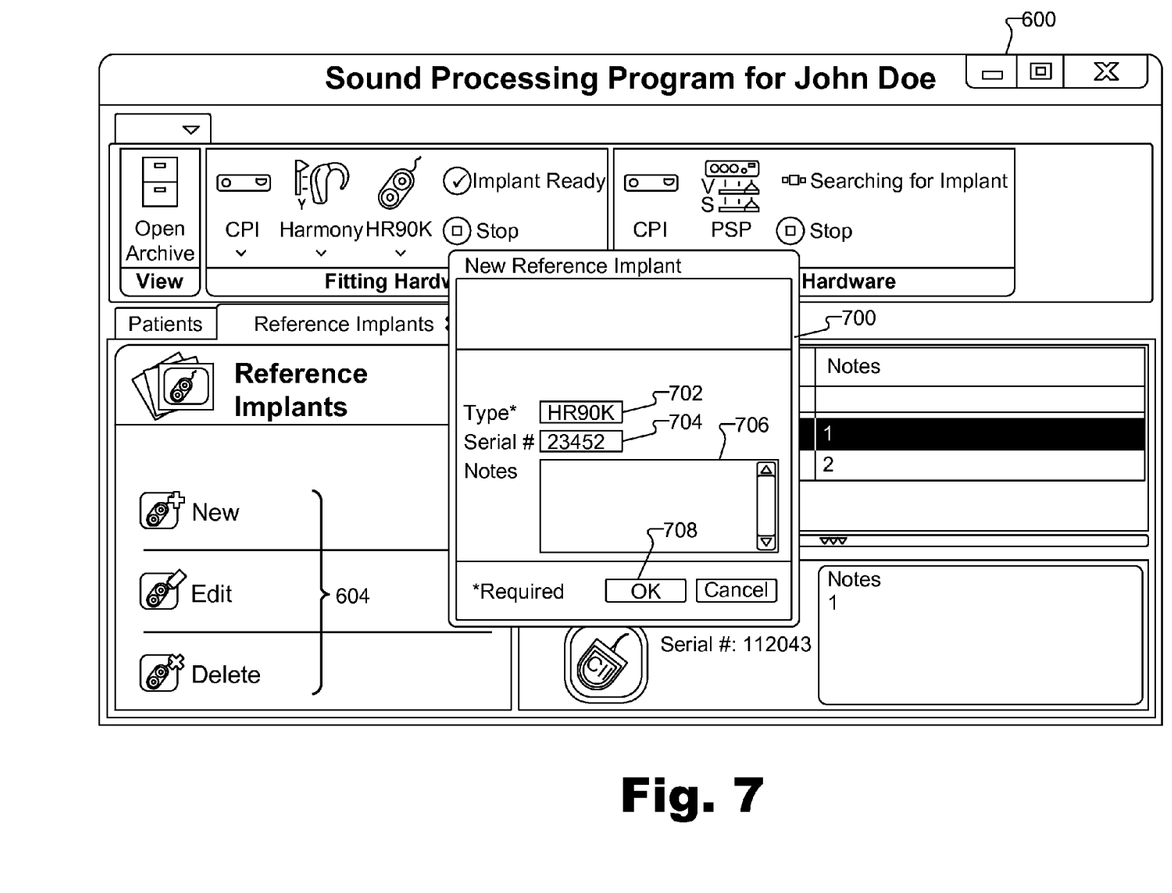

Various exemplary registration GUIs will now be described in reference to FIGS. 6-7. FIG. 6 illustrates a registration GUI 600 configured to provide a user with one or more tools for managing reference implants. As shown in FIG. 6, GUI 600 may include a list 602 of registered reference implants. GUI 600 may also include a set of selectable options 604. In FIG. 6, the set of selectable options 604 includes a "new" option that may be selected to request that a new reference implant be registered, an "edit" option that may be selected to request that a selected registered reference implant be edited, and a "delete" option that may be selected to request that a selected registered reference implant be deleted (i.e., unregistered).

In response to a user selection of the "new" option shown in FIG. 6, fitting subsystem 102 may initiate a registration process and perform one or more registration operations to register a new reference implant with fitting subsystem 102. For example, fitting subsystem 102 may display GUI 700 as shown in FIG. 7. GUI 700 may include one or more fields, including a "type" field 702 that may be populated with data indicating a type of the new reference implant being registered (e.g., data indicating a make, model, and/or manufacturer of the new reference implant), a "serial #" field 704 that may be populated with data representative of a unique identifier associated with the new reference implant being registered, and a "notes" field 706 that may be populated with information related to the new reference implant being registered.

In certain embodiments, one or more of the fields in GUI 700 may be populated by a user providing input into GUI 700. For example, the user may manually enter information into one or more of the fields in GUI 700. Additionally or alternatively, one or more of the fields in GUI 700 may be automatically populated by fitting subsystem 102. For example, if the new reference implant being registered is coupled to fitting subsystem 102, fitting subsystem 102 may request and acquire data from the new reference implant. The data may indicate a type and/or a unique identifier associated with the new reference implant. Fitting subsystem 102 may populate fields 702 and/or 704 with the acquired data.

With one or more of the fields in GUI 700 populated, a user may select an "OK" button 708 in GUI 700. In response, fitting subsystem 102 may register the new reference implant in any of the ways described herein.

In certain embodiments, fitting subsystem 102 may be configured to prompt a user to assign a registered reference implant that is coupled to fitting subsystem 102 to emulate either a right-side implantable cochlear device or a left-side implantable cochlear device. In some examples, fitting subsystem 102 may be configured to automatically prompt the user to make this assignment each time a registered reference implant is coupled to fitting subsystem 102.

Figure 8:
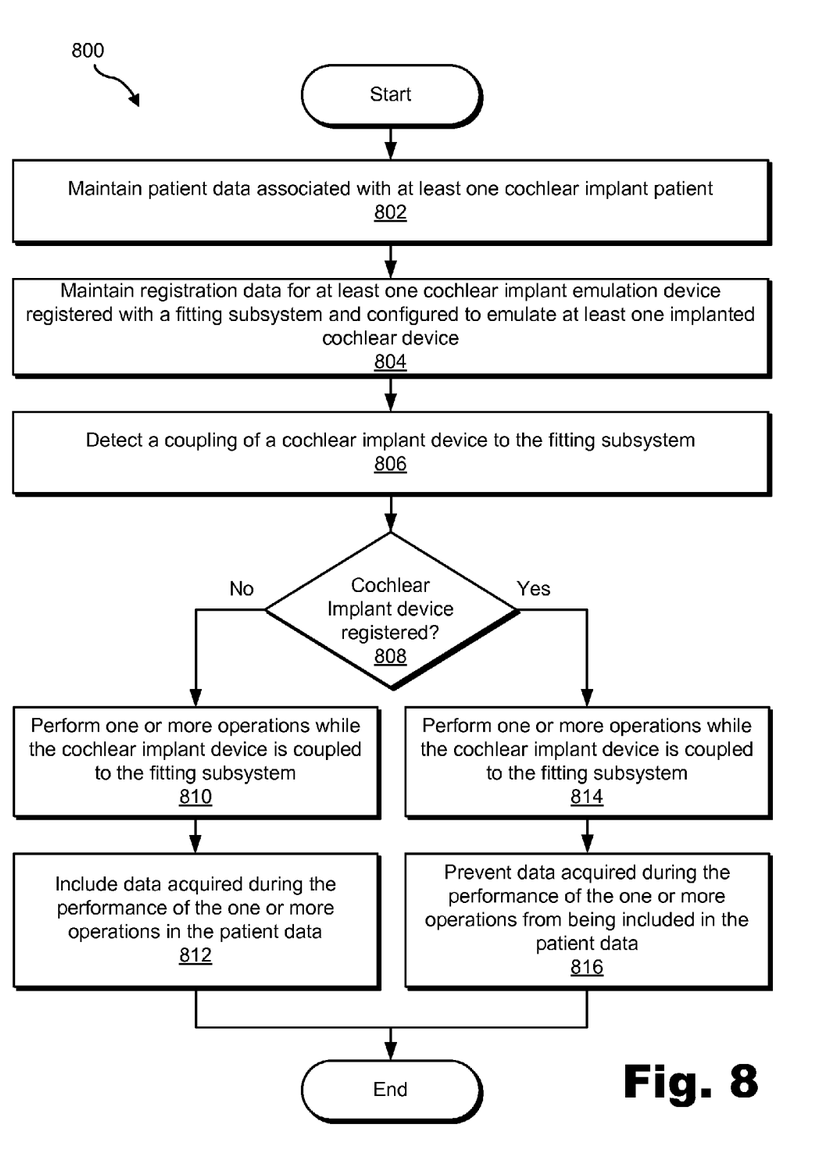
FIG. 8 illustrates an exemplary method of identifying a cochlear implant device and managing data associated therewith.

FIG. 8 illustrates an exemplary method 800 of identifying a cochlear implant device and managing data associated therewith. While FIG. 8 illustrates exemplary steps according to one embodiment, other embodiments may omit, add to, reorder, combine, and/or modify any of the steps shown in FIG. 8. One or more of the steps shown in FIG. 8 may be performed by any component or combination of components of fitting subsystem 102.

In step 802, fitting subsystem 102 may maintain patient data associated with at least one cochlear implant patient. Step 802 may be performed in any of the ways described above.

In step 804, fitting subsystem 102 may maintain registration data for a least one cochlear implant emulation device registered with fitting subsystem 102 and configured to emulate at least one implanted cochlear device. The registration data may be maintained in any suitable way. For example, the registration data may be maintained as a table of unique identifiers representative of cochlear implant emulation devices registered with fitting subsystem 102.

In step 806, fitting subsystem 102 may detect a coupling of a cochlear implant device to fitting subsystem 102. Step 806 may be performed in any of the ways described above. Upon initial detection of a coupling of the cochlear implant device to fitting subsystem 102, fitting subsystem 102 has not yet determined whether the coupled cochlear implant device is a registered cochlear implant emulation device configured to emulate an implanted cochlear device.

In step 808, fitting subsystem 102 may automatically determine, based on the registration data maintained in step 804, whether the coupled cochlear implant device is registered with fitting subsystem 102. The determination may be made in any suitable way. For example, fitting subsystem 102 may obtain a unique identifier from the coupled cochlear implant device and search the registration data maintained in step 804 for a matching unique identifier. If the registration data includes a matching unique identifier, fitting subsystem 102 may determine that the coupled cochlear implant device is registered with fitting subsystem 102. Conversely, if the registration data does not include a matching unique identifier, fitting subsystem 102 may determine that the coupled cochlear implant device is not registered with fitting subsystem 102.

If fitting subsystem 102 determines in step 808 that the coupled cochlear implant device is not registered (No; step 808), processing may continue from step 808 to step 810. In step 810, fitting subsystem 102 may perform one or more operations while the cochlear implant device is coupled to fitting subsystem 102. The operations may include any of the operations described herein, including, for example, one or more troubleshooting operations.

In step 812, fitting subsystem 102 may include data acquired during the performance of the one or more operations in the patient data maintained in step 802. Accordingly, as described above, the data acquired during the performance of the one or more operations may be utilized by fitting subsystem 102 in one or more subsequent operations. After step 812, method 800 ends.

If, however, in step 808, fitting subsystem 102 determines that the coupled cochlear implant device is registered (Yes; step 808), processing may continue from step 808 to step 814. In step 814, fitting subsystem 102 may perform one or more operations while the cochlear implant device is coupled to fitting subsystem 102. The operations may include any of the operations described herein, including one or more troubleshooting operations.

In step 816, fitting subsystem 102 may prevent data acquired during the performance of the one or more operations in step 814 from being included in the patient data maintained in step 802. Step 816 may be performed in any suitable way. For example, fitting subsystem 102 may segregate the data acquired during the performance of the one and more operations in step 814 from the patient data maintained in a database by fitting subsystem 102. Accordingly, data acquired during operations performed while a registered cochlear implant emulation device is coupled to fitting subsystem 102 may be processed in a way that avoids polluting the patient data with data associated with the cochlear implant emulation device. After step 816, method 800 ends.

One or more steps of method 800 may be repeated each time a cochlear implant device is coupled to fitting subsystem 102. For example, another cochlear implant device may be coupled to fitting subsystem 102, and fitting subsystem 102 may perform, for the other cochlear implant device, steps 806 and 808 followed by either steps 810 and 812 if the other cochlear implant device is not registered or steps 814 and 816 if the other cochlear implant device is registered.

In certain embodiments, fitting subsystem 102 may be configured to introduce an exception into method 800 when operations are performed for a patient that is labeled as a "test patient" in the patient data. To illustrate, a test patient may be created and represented in the patient data. The test patient may be utilized as may suit a particular implementation, including for testing fitting subsystem 102 and/or cochlear implant subsystem 104. When operations are performed for the test patient, fitting subsystem 102 may allow data acquired during the performance of the operations while a cochlear implant emulation device is coupled to fitting subsystem 102 to be included in the patient data for the test patient.

In certain embodiments, one or more of the components and/or processes described herein may be implemented and/or performed by one or more appropriately configured computing devices. To this end, one or more of the systems and/or components described above may include or be implemented by any computer hardware and/or computer-implemented instructions (e.g., software) embodied on a non-transitory computer-readable medium configured to perform one or more of the processes described herein. In particular, system components may be implemented on one physical computing device or may be implemented on more than one physical computing device. Accordingly, system components may include any number of computing devices, and may employ any of a number of computer operating systems.

In certain embodiments, one or more of the processes described herein may be implemented at least in part as instructions executable by one or more computing devices. In general, a processor (e.g., a microprocessor) receives instructions, from a tangible computer-readable medium, (e.g., a memory, etc.), and executes those instructions, thereby performing one or more processes, including one or more of the processes described herein. Such instructions may be stored and/or transmitted using any of a variety of known non-transitory computer-readable media.

A non-transitory computer-readable medium (also referred to as a processor-readable medium) includes any non-transitory medium that participates in providing data (e.g., instructions) that may be read by a computer (e.g., by a processor of a computer). Such a non-transitory medium may take many forms, including, but not limited to, non-volatile media and/or volatile media. Non-volatile media may include, for example, optical or magnetic disks and other persistent memory. Volatile media may include, for example, dynamic random access memory ("DRAM"), which typically constitutes a main memory. Common forms of non-transitory computer-readable media include, for example, a floppy disk, flexible disk, hard disk, magnetic tape, any other magnetic medium, a CD-ROM, DVD, any other optical medium, a RAM, a PROM, an EPROM, a FLASH-EEPROM, any other memory chip or cartridge, or any other non-transitory medium from which a computer can read.

Figure 9:
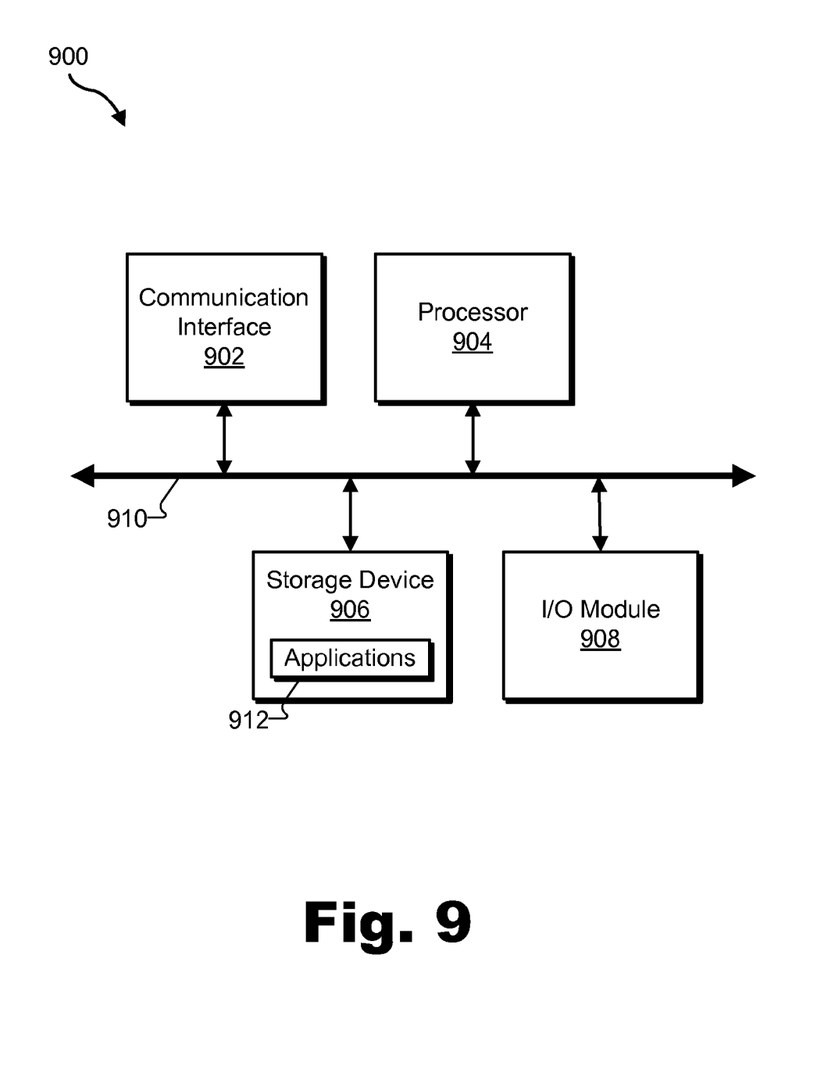
FIG. 9 illustrates an exemplary computing device according to principles described herein.

FIG. 9 illustrates an exemplary computing device 900 that may be configured to perform one or more of the processes described herein. As shown in FIG. 9, computing device 900 may include a communication interface 902, a processor 904, a storage device 906, and an input/output ("I/O") module 908 communicatively connected via a communication infrastructure 910. While an exemplary computing device 900 is shown in FIG. 9, the components illustrated in FIG. 9 are not intended to be limiting. Additional or alternative components may be used in other embodiments. Components of computing device 900 shown in FIG. 9 will now be described in additional detail.

Communication interface 902 may be configured to communicate with one or more computing devices. Examples of communication interface 902 include, without limitation, a wired network interface (such as a network interface card), a wireless network interface (such as a wireless network interface card), a modem, and any other suitable interface. Communication interface 902 may additionally or alternatively provide such a connection through, for example, a local area network (such as an Ethernet network), a personal area network, a telephone or cable network, a satellite data connection, a dedicated URL, or any other suitable connection. Communication interface 902 may be configured to interface with any suitable communication media, protocols, and formats, including any of those mentioned above.

Processor 904 generally represents any type or form of processing unit capable of processing data or interpreting, executing, and/or directing execution of one or more of the instructions, processes, and/or operations described herein. Processor 904 may direct execution of operations in accordance with one or more applications 912 or other computer-executable instructions such as may be stored in storage device 906 or another non-transitory computer-readable medium.

Storage device 906 may include one or more data storage media, devices, or configurations and may employ any type, form, and combination of data storage media and/or device. For example, storage device 906 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 906. For example, data representative of one or more executable applications 912 (which may include, but are not limited to, one or more of the software applications described herein) configured to direct processor 904 to perform any of the operations described herein may be stored within storage device 906. In some examples, data may be arranged in one or more databases residing within storage device 906.

I/O module 908 may be configured to receive user input and provide user output and may include any hardware, firmware, software, or combination thereof supportive of input and output capabilities. For example, I/O module 908 may include hardware and/or software for capturing user input, including, but not limited to, a keyboard or keypad, a touch screen component (e.g., touch screen display), a receiver (e.g., an RF or infrared receiver), and/or one or more input buttons.

I/O module 908 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 908 is configured to provide graphical data to a display for presentation to a user. The graphical data may be representative of one or more graphical user interfaces and/or any other graphical content as may serve a particular implementation.

In some examples, any of the facilities and/or subsystems described herein may be implemented by or within one or more components of computing device 900. For example, one or more applications 912 residing within storage device 906 may be configured to direct processor 904 to perform one or more processes or functions associated with communication facility 402, user interface facility 404, fitting facility 406, and registration facility 408. Likewise, storage facility 412 may be implemented by or within storage device 906.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
    maintaining, by a fitting subsystem, patient data associated with a cochlear implant patient and representative of information associated with one or more components of a cochlear implant subsystem fitted to the patient;
    maintaining, by the fitting subsystem, registration data for a cochlear implant emulation device registered with the fitting subsystem and configured to emulate an implanted cochlear device included in the cochlear implant subsystem, wherein the cochlear implant emulation device is not implanted within the cochlear implant patient and is bundled with a resistive load configured to emulate an actual load of the implanted cochlear device;
    detecting, by the fitting subsystem, a coupling of a cochlear implant device to the fitting subsystem;
    automatically determining, by the fitting subsystem based on the registration data, that the coupled cochlear implant device is the cochlear implant emulation device registered with the fitting subsystem;
    performing, by the fitting subsystem, one or more operations while the cochlear implant emulation device is coupled to the fitting subsystem;
    determining, by the fitting subsystem based on the one or more operations, that the cochlear implant subsystem functions incorrectly while the implanted cochlear device is coupled to the fitting subsystem and correctly while the cochlear implant emulation device is coupled to the fitting subsystem;
    indicating, by the fitting subsystem based on the determining, that the implanted cochlear device is a source of a problem with the cochlear implant subsystem; and
    preventing, by the fitting subsystem, data acquired by the fitting subsystem during the performance of the one or more operations while the cochlear implant emulation device is coupled to the fitting subsystem from being included in the patient data.

2. The method of claim 1, further comprising:
    detecting, by the fitting subsystem, a coupling of another cochlear implant device to the fitting subsystem;
    automatically determining, by the fitting subsystem based on the registration data, that the coupled another cochlear implant device is not registered with the fitting subsystem;
    performing, by the fitting subsystem, one or more operations while the another cochlear implant device is coupled to the fitting subsystem; and
    including, by the fitting subsystem, data acquired by the fitting subsystem during the performance of the one or more operations while the another cochlear implant device is coupled to the fitting subsystem in the patient data.

3. The method of claim 2, further comprising:
    utilizing, by the fitting subsystem, the patient data to perform one or more fitting operations to fit the another cochlear implant device to the cochlear implant patient.

4. The method of claim 1, wherein the registration data includes a unique identifier associated with the cochlear implant emulation device.

5. The method of claim 1, wherein the automatically determining comprises searching the registration data for the unique identifier associated with the cochlear implant emulation device.

6. The method of claim 1, wherein the one or more operations performed while the cochlear implant emulation device is coupled to the fitting subsystem comprise at least one of a diagnostic operation and a troubleshooting operation.

7. The method of claim 1, wherein the preventing comprises segregating the data acquired by the fitting subsystem during the performance of the one or more operations while the cochlear implant emulation device is coupled to the fitting subsystem from the patient data.

8. The method of claim 1, wherein the coupling comprises an establishment of a communication link between the cochlear implant device and a headpiece that is communicatively coupled to the fitting subsystem by way of a sound processor.

9. The method of claim 1, further comprising:
   receiving, by the fitting subsystem, a request to register the cochlear implant emulation device with the fitting subsystem;
   obtaining, by the fitting subsystem by way of the coupling, a unique identifier for the cochlear implant emulation device; and
   registering, by the fitting subsystem, the cochlear implant emulation device with the fitting subsystem, the registering including storing the unique identifier in the registration data.

10. The method of claim 1, further comprising providing, by the fitting subsystem, a graphical user interface configured to facilitate a registration of the cochlear implant emulation device with the fitting subsystem.

11. The method of claim 1, embodied as computer-executable instructions on at least one non-transitory computer-readable medium.

12. A system comprising:
   a registration facility that maintains registration data for a registered cochlear implant emulation device configured to emulate an implanted cochlear device included in a cochlear implant subsystem fitted to a cochlear implant patient, wherein the registered cochlear implant emulation device is not implanted within the cochlear implant patient and is bundled with a resistive load configured to emulate an actual load of the implanted cochlear device; and
   a fitting facility communicatively coupled to the registration facility and configured to
      maintain patient data associated with the cochlear implant patient and representative of information associated with one or more components of the cochlear implant subsystem fitted to the patient,
      detect a coupling of a cochlear implant device,
      automatically determine, based on the registration data, that the coupled cochlear implant device is the registered cochlear implant emulation device,
      perform one or more operations while the cochlear implant emulation device is coupled,
      determine, based on the one or more operations, that the cochlear implant subsystem functions incorrectly while the implanted cochlear device is coupled to the fitting subsystem and correctly while the cochlear implant emulation device is coupled to the fitting subsystem,
      indicate, based on the determining, that the implanted cochlear device is a source of a problem with the cochlear implant subsystem, and
      prevent data acquired by the fitting facility during the performance of the one or more operations while the cochlear implant emulation device is coupled from being included in the patient data.

13. The system of claim 12, wherein:
   the registration data includes a unique identifier associated with the cochlear implant emulation device; and
   the fitting facility is configured to automatically determine that the coupled cochlear implant device is the registered cochlear implant emulation device by searching the registration data for the unique identifier associated with the cochlear implant emulation device.

* * * * *